United States Patent [19]

Stancik, Jr.

[11] Patent Number: 4,817,590

[45] Date of Patent: Apr. 4, 1989

[54] CAST AND METHOD OF ASSEMBLY ON A LIMB

[76] Inventor: William C. Stancik, Jr., 1019 Felder Ave., Montgomery, Ala. 36106

[21] Appl. No.: 37,391

[22] Filed: Apr. 9, 1987

[51] Int. Cl.4 .............................................. A61F 5/04
[52] U.S. Cl. .............................. 128/90; 128/DIG. 20
[58] Field of Search ................... 128/89 R, 90, 91 R, 128/87 R, DIG. 20

[56] References Cited

U.S. PATENT DOCUMENTS

| | | | |
|---|---|---|---|
| Re. 27,957 | 4/1974 | Larson | 128/89 R |
| 3,032,033 | 5/1962 | Ramirez | 128/90 |
| 3,301,252 | 1/1967 | Machoney, Jr. | 128/90 |
| 3,563,234 | 2/1971 | Umstead | 128/90 |
| 3,631,854 | 1/1972 | Fryer | 128/90 |
| 3,643,656 | 2/1972 | Young et al. | 128/90 |
| 3,930,496 | 1/1976 | Gibbons | 128/90 |
| 3,998,219 | 12/1976 | Mercer | 128/89 R |
| 4,060,075 | 11/1977 | Blomer et al. | 128/90 |
| 4,306,549 | 12/1981 | Canie | 128/90 |
| 4,309,990 | 1/1982 | Brooks et al. | 128/90 |
| 4,483,332 | 11/1984 | Rind | 128/89 R |
| 4,530,352 | 7/1985 | Halloway | 128/89 R |
| 4,538,601 | 9/1985 | Barker | 128/89 R |
| 4,657,921 | 10/1986 | Seeler | 128/89 R |

Primary Examiner—Dalton L. Truluck
Attorney, Agent, or Firm—Fleit, Jacobson, Cohn & Price

[57] ABSTRACT

A cast for placement on a limb or other portion of the human anatomy in the event of a bone fracture or other injury for maintaining the enclosed portion of the limb or human anatomy immobilized while the bone fracture or other injury is healing. More specifically, a cast is provided in which flowable, liquid material may be injected at least once or at different time intervals during the healing period in order to maintain an optimum fitting relationship between the cast and the limb or human anatomy for maintaining optimum alignment stability and immobilization throughout the healing period. A low density, hardenable, liquid plastic material such as expandable polyurethane foam is injected between a stocking or other buffer which engages the limb or other portion of the human anatomy and a fabric wrap or a liner of other material forming an inner layer of a conventional plaster cast or a fiberglass reinforced cast with the liquid material being injected into this area by the use of a syringe with an attached tube that is inserted into the cast to the inner end thereof with the tube being gradually pulled out of the cast to fill and evenly distribute foam in the space between the cast and limb to fill any space resulting from reduction in size of the limb or human anatomy thereby maintaining optimum fit between the cast and limb or human anatomy and thus maintaining optimum alignment, stability and immobilization of a fractured limb or the like.

4 Claims, 1 Drawing Sheet

CAST AND METHOD OF ASSEMBLY ON A LIMB

BACKGROUND OF THE INVENTION

Field of the Invention

The present invention generally relates to a cast for placement on a limb or other portion of the human anatomy in the event of a bone fracture or other injury for maintaining the enclosed portion of the limb or human anatomy immobilized while the bone fracture or other injury is healing. More specifically, a cast is provided in which flowable, liquid material may be injected at least once or at different time intervals during the healing period in order to maintain an optimum fitting relationship between the cast and the limb or human anatomy for maintaining optimum alignment, stability and immobilization throughout the healing period. A low density, hardenable, polyurethane foam plastic material is injected between a stocking which engages the limb or other portion of the human anatomy and a fabric wrap forming an inner layer of a conventional plaster cast or a fiberglass reinforced cast with the liquid material being injected into this area by the use of a large syringe (140 cc) having a long tube that is constructed along the posterior portion of the cast. The tube will be gradually pulled upwardly and withdrawn from the cast as the polyurethane foam is injected to provide even distribution of the foam thereby completely filling any space resulting from reduction in size of the limb or any other event which loosens the cast thereby maintaining optimum fit between the cast and limb or human anatomy and thus maintaining optimum alignment, stability and immobilization of a fractured limb or the like.

Information Disclosure Statement

Immobilization of a fractured limb during the healing period has been practiced for many years with a hardenable material such as plaster being placed on the limb after the fractured bone or bones have been properly aligned and positioned in order to stabilize the limb during the healing period. One of the ongoing problems with conventional procedures is the reduction in the size of the fractured limb during the healing period which may be as long as 8 to 10 weeks. Conventionally, three casts are used with the first cast being replaced after swelling associated with the break subsides and the original cast becomes too loose to support the fracture site. The second cast is then replaced when atrophy of the limb muscles occurs thereby resulting in looseness of the cast so that it does not optimally support the fracture site. While various types of casts are known as exemplified by the prior art to be filed with a separate Information Disclosure Statement, the prior art does not contemplate the injection of a hardenable material interiorly of an existing cast at periodic intervals or at least once per cast during the healing period to maintain optimum fitting relationship between the cast and limb for supporting and immobilizing the fracture site.

SUMMARY OF THE INVENTION

An object of the present invention is to provide a cast for a limb having a fractured bone or bones therein in which a flowable, liquid, low density, hardenable material is injected into the space between an existing cast and a limb which is reduced in size during the healing period in order to maintain optimum supporting and stabilizing relation between the cast and fracture site for maintaining alignment and optimum position of the bone or bones during the healing period.

Another object of the invention is to provide a method of maintaining optimum stability and immobilization of a fracture site by at least once or periodically injecting a hardenable material between an existing rigid cast and the exterior of a fracture site to fill any space between the existing cast and a limb which has been reduced in size due to reduction in swelling, atrophy and the like.

A further object of the invention is to provide a cast and method of maintaining optimum fit between the cast and a fracture site which includes the injection of liquid hardenable material such as polyurethane foam having low density characteristics from a large syringe with an attached tube to be gradually pulled up and out of the cast to permit even distribution of the foam in the space between a covering stocking for the limb or fracture site and the interior of an existing rigid cast in order to fill this space by expanding and molding so that when the hardenable material hardens, the hardened material combined with the existing cast will effectively stabilize the fracture site and maintain alignment and position of the fractured bone or bones.

These together with other objects and advantages which will become subsequently apparent reside in the details of construction and operation as more fully hereinafter described and claimed, reference being had to the accompanying drawings forming a part hereof, wherein like numerals refer to like parts throughout.

DESCRIPTION OF THE PREFERRED EMBODIMENT

Figure 1:
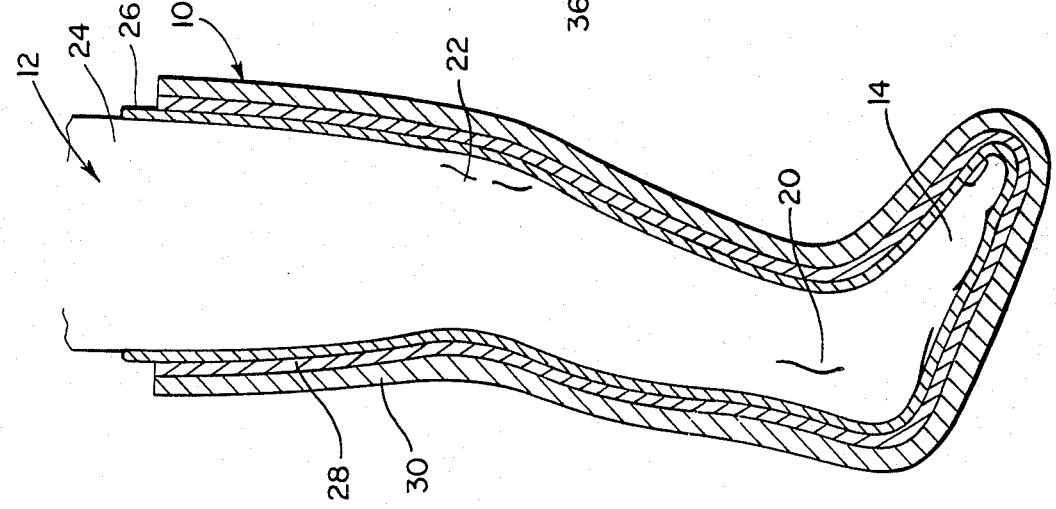
FIG. 1 is a sectional view of a conventional cast placed upon a limb in bridging relation to a fracture site.
Figure 2:
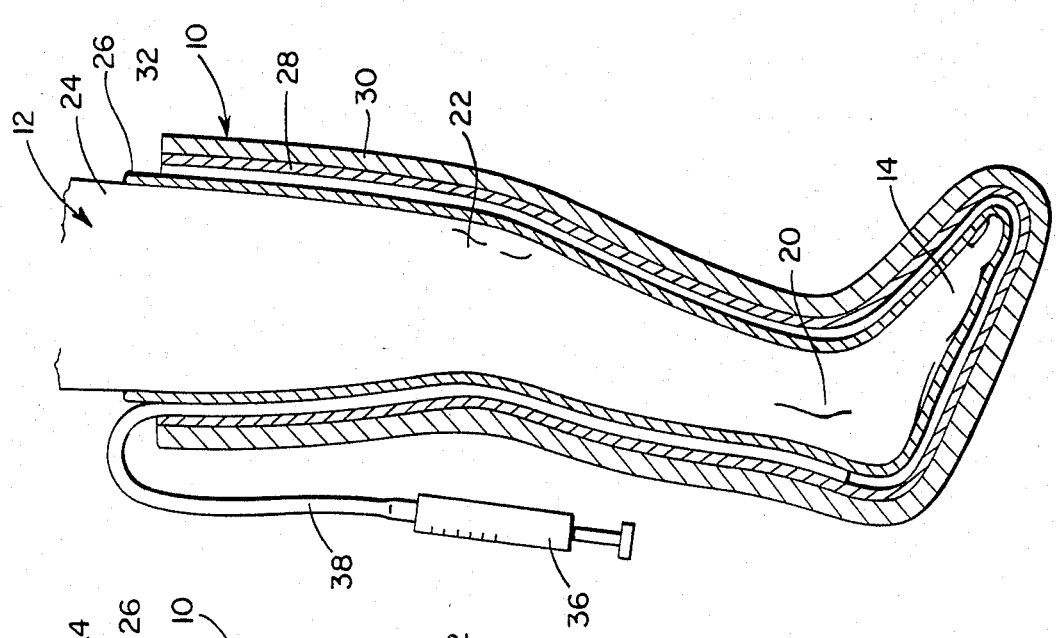
FIG. 2 is a sectional view similar to FIG. 1 illustrating the existence of a space which occurs between the limb and cast when the limb reduces in size such as when swelling is reduced or when the limb muscles atrophy due to non-use and illustrating the space being filled with a hardenable, liquid, low density material from a syringe having a long tube associated therewith.
Figure 3:
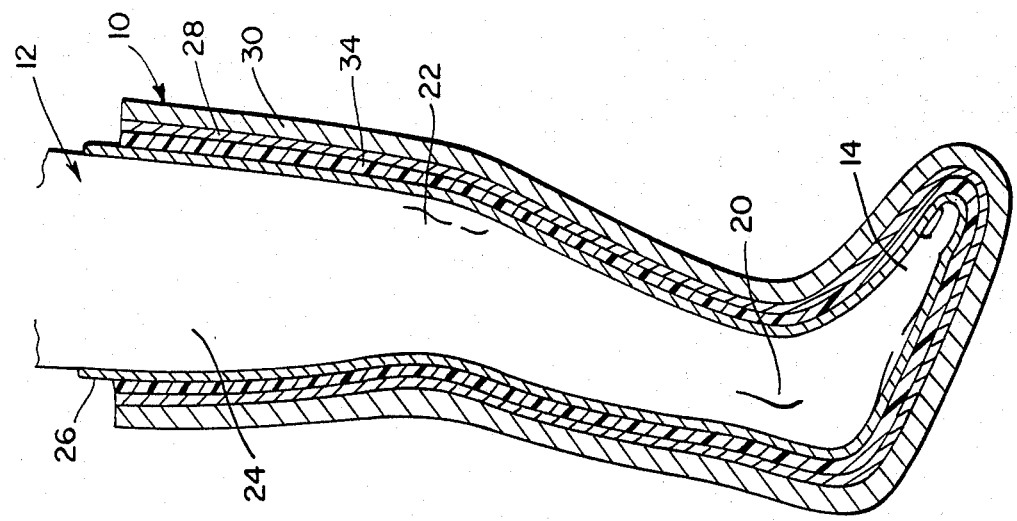
FIG. 3 is a sectional view similar to FIGS. 1 and 2 but illustrating the space filled with supportive material.

Referring now specifically to the drawings, a conventional cast is generally designated by the numeral 10 and is placed on the leg or limb 12 so that it encloses the foot 14, ankle area 20, knee area 22 and a portion of the upper leg 24 with it being pointed out that the cast 10 could also be placed on only a lower portion of the leg, on the arm or on other areas of the human anatomy which have suffered a fracture or other injury where it is desirable to maintain the fracture site or injury site immodilized with components of the human anatomy properly aligned and positioned. The cast 10 includes a stocking 26 positioned over the foot and leg and usually is of fabric material and is resilient so that it closely conforms with and engages the exterior surface of the limb 12. Exteriorly of the stocking 26, there is provided a fabric wrap 28 of cotton or similar fabric material which is positioned between the stocking 26 and an exterior layer of plaster 30 or other hardenable material conventionally employed in forming a cast such as fiber reinforced plastic or other materials employed for immobilizing a fracture site in order to maintain alignment of and position of bones that have been fractured so that they will be properly joined.

As is well known, when a cast is first placed on a limb that has suffered a fracture, the limb will be somewhat swollen and once the swelling has subsided, there will be a space 32 between the stocking 26 and cotton wrap 28 with this space extending throughout the area of the limb 12 which has the fracture site. Thus, the reduction in the swelling results in a reduction in the size of the limb 12, thus forming a space 32. In order to maintain optimum alignment and support of the fracture site, the space 32 is filled with a liquid, flowable, hardenable low density material 34 that may be supplied from a large syringe 36 having a reduced cross sectional area discharge flexible tube 38 which can be constructed into or inserted into the posterior portion of the leg cast or along any limb where muscles have atrophied. The tube 38 will be gradually pulled up and out as the foam is injected for evenly distributing the foam so that the hardenable material 34 will completely fill the space 32 from top to bottom and circumferentially thereby resulting in the cast 10 being adjusted or tightened so that it maintains optimum alignment and stability of the fractured limb throughout the healing period.

As indicated, this procedure can be initiated as soon as the swelling subsides and/or after passage of several weeks when a space 32 again occurs due to atrophy of the muscles of the limb due to non-use thereby eliminating the necessity of completely replacing the cast at least once during the healing period thereby eliminating possible movement of the fracture site which can occur when a cast is being removed since a cast saw has to be manipulated which an result in forces being applied to the fracture site. Also, it is difficult to replace an existing cast with a properly fitting new cast without introducing undesired forces to the fracture site. Thus, with the method and apparatus, the original cast may be left in position during the entire healing period and, in effect, tightened or adjusted to maintain optimum fit, alignment and stability at several intervals during the healing period in a simple and effective manner by injecting an expandable polyurethane foam or similar low density, hardenable, flowable material through tube 38 placed along the posterior portion of the limb or muscled area and the tube 38 is pulled up and out to uniformly fill space 32. In the event the space 32 is not closed at the bottom such as when a generally cylindrical cast is provided, a closure tape or the like may be provided for the bottom of the space to maintain the flowable material in place while it hardens.

By injecting the liquid, hardenable material between the stocking 26 and the cotton wrap 28 or some other buffer that will prevent the polyurethane foam from touching the skin approximately 3 days after the date of the fracture when looseness occurs due to the fracture swelling subsiding and/or again 6 to 7 weeks after the fracture data when looseness due to atrophy occurs, near perfect alignment and stability of the fracture site will have been maintained throughout the convalescing or healing period. Optionally, the polyurethane may be injected only once during the healing period. Thus, this method not only provides a more efficient and better healing procedure but also will save patients time and money since the orthopedist will not have to remove an existing cast and replace it with a new cast. In some instances, it may be necessary to provide only a single injection after the original cast is placed on the limb such as when very little swelling occurs as a result of the fracture or when reduction in size of the limb is minimal due to atrophy. Several low density foam plastic materials may be used to fill the space 32 with the density, specific gravity and strength characteristics of such material satisfying the requirements of the particular use of the material. Also, other flowable materials may be used which are capable of providing adequate support to the limb which has a fracture site. An example of such material is a gel which will solidify sufficiently for adequate and stable support but will not become completely rigid.

The foregoing is considered as illustrative only of the principles of the invention. Further, since numerous modifications and changes will readily occur to those skilled in the art, it is not desired to limit the invention to the exact construction and operation shown and described, and accordingly, all, suitable modifications and equivalents may be resorted to, falling within the scope of the invention.

I claim:

1. A cast for immobilizing and stabilizing a fracture site comprising a rigid outer shell of unitary construction of hardenable material adapted to conform with, support and stabilize a fracture site at the time of an original fracture when the limb is swollen, a buffer adapted to be positioned between the cast and limb, said buffer being resilient and adapted to snugly engage the exterior of the limb and adapted to follow the limb away from the cast as the limb reduces in cross-sectional area, a liner on the inner surface of said rigid cast in engagement with the buffer when the cast is initially applied to a swollen limb with the liner staying against the inner surface of the cast, and a filler of flowable and hardenable material adapted to support the limb and adapted to be injected into and fill the space between the liner on the inner surface of the rigid cast and the buffer which followed the limb as the limb reduced in size due to reduction in swelling or atrophy of the muscles for maintaining optimum support and stability of the fracture site subsequent to the rigid cast being placed on the fracture site.

2. The structure as defined in claim 1 wherein said buffer is a stocking adapted to engage the limb, said liner being a fabric wrap and said filler being polyurethane foam.

3. The method of maintaining optimum alignment and positioning of a fractured bone during a healing period consisting of the steps of accurately aligning and positioning the broken bone, applying a rigid cast to the fracture site to maintain alignment and positioning of the bone and injecting a flowable, hardenable material capable of supporting the fracture site interiorly of the cast at least once subsequent to application of the cast and subsequent to reduction in size of the fracture site due to reduction in swelling of the fracture site or reduction of the cross-sectional area of the fracture site due to atrophy of muscle and tissue thereby maintaining optimum alignment and position of the bone and stabilization thereof throughout the healing period, said step of injecting material including the step of filling a space between the fracture site and cast at least twice during the healing process with the first filling occurring several days after the fracture when swelling of the fracture site has subsided and the second filling occurring several weeks after the original fracture due to reduction in size of the fracture site due to atrophy thereby eliminating the necessity of replacing an original cast with a totally new cast subsequent to application of the original cast.

4. The method of maintaining optimum alignment and positioning of a fractured bone during a healing period consisting of the steps of accurately aligning and positioning the broken bone, applying a rigid cast to the fracture site to maintain alignment and positioning of the bone and injecting a flowable, hardenable material capable of supporting the fracture site interiorly of the cast at least once subsequent to application of the cast and subsequent to reduction in size of the fracture site due to reduction in swelling of the fracture site or reduction of the cross-sectional area of the fracture site due to atrophy of muscle and tissue thereby maintaining optimum alignment and position of the bone and stabilization thereof throughout the healing period, said injection step including the injection of low density polyurethane foam which expands and solidifies, said step of applying a rigid cast including the step of applying a buffer stocking of resilient material snugly around the limb prior to placing the rigid cast on the limb, said injection step including the injection of said foam between the cast and buffer stocking.

* * * * *